United States Patent [19]

Holtkamp, Sr.

[11] Patent Number: Plant 7,008

[45] Date of Patent: Aug. 29, 1989

[54] AFRICAN VIOLET PLANT NAMED KNOXVILLE

[76] Inventor: Reinhold Holtkamp, Sr., Werther Strasse 112, D4294 Isselburg, Fed. Rep. of Germany

[21] Appl. No.: 251,323

[22] Filed: Sep. 30, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Knoxville which is a sport of Nashville, disclosed in U.S. Plant Pat. No. 4,553. Knoxville is characterized by its single, pink flowers with frilled edges and darker pink center radiating into the 2 smaller petals; strong, upright flower stems that curve toward the center to form a bouquet above the leaves; medium green, serrated girl-type leaves with bright light green center; profuse flowering, vigorous growth habit, flowering 10–11 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Knoxville.

The new cultivar was referred to during the breeding and selection process by the designation M/d 150/2, and is a sport of Nashville, disclosed in my U.S. Plant Pat. No. 4,553 granted May 6, 1980. Knoxville is similar in all essential respects to Nashville except for its pink flower color.

Knoxville was discovered in a flowering block of the parent cultivar Nashville, and subsequently selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Knoxville has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Knoxville, which in combination distinguish this African violet as a new and distinct cultivar:

(1) Strong, upright flower stems curving toward the center.
(2) Single, pink flowers with frilled edges.
(3) Profuse flowering
(4) Each plant carries 8–9 and more upright flower stems, each of which carries 7–9 and more flowers.
(5) Long lasting, non-dropping flowers.
(6) Vigorous grower.
(7) Plant saleable 10 to 11 weeks after potting.
(8) Seed capsules push slightly through.
(9) Medium green girl-type leaves, wavy, with a bright light green center radiating along the veins; serrated.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 2 p.m. in Nashville, Tenn.

Botanical classification: *Saintpaulia ionantha,* Ramat., c.v. Knoxville.

Parentage: Sport of Nashville, disclosed in U.S. Plant Pat. No. 4,553.

Propagation: The new cultivar holds its distinguishing characteristics through successive propagations by leaf cuttings.

Plant: From 8 cm to 10 cm tall when grown in pots, and approximately 18–20 cm in diameter when fully grown.

*Leaves.*—General form: Round to oval, girl-type. Diameter: 60–65 mm. Texture: Velvety. Aspect: Shiny, wavy, serrated, hairy, bright light green center radiating along the veins. Veins: Upperside: well visible, greenish white radiating from the center; underside: very well pronounced, light green, shiny. Color (upperside): Yellow-Green Group 147 A, center 145 D. Color (underside): Greyed-Green Group 194 C. Petiole: Strong upright, light green with purplish touch, hairy.

*Flowers.*—Buds: Ball-shaped, 7–8 mm just before opening, light pink, hairy. Sepals: Five (5). Color: Green with purplish brown touch. Calyx: Shape: Funnel-shaped. Aspect: Spear-shaped, hairy. Peduncle: Character: Strong upright, hairy. Color: Purplish green.

*Individual flowers.*—Size: 40–45 mm. Shape: Single violet-shaped (3 large and 2 small petals). Color (upperside): Red-Purple Group 74 D and lighter, center 74 C. Under cooler temperature and more intensive lighting, the pink tends to intensify. Color (underside): Red-Purple Group 74 D and lighter. Borne: Each flower stem carries 7–9 and more flowers on strong, upright peduncles that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish green with pink traces, b 4 mm long. Pollen color: Yellow Group 7 A. Styles: 7 mm long, dark pink, base of ovary light green and hairy. p2 *Roots.*—Normally developed, white when young, turning slightly brownish when older.

Disease resistance: Good.

General observations: Knoxville has a very attractive appearance due to its medium green, serrated leaves with a bright light green center radiating along the veins. A tight bouquet of flowers free standing above the leaves develops after approximately 10–11 weeks.

Each of the 8–9 and more flowers stems carries 7–9 and more single pink, violet-shaped flowers with frilled edges. The flowers display a much darker pink in the center that radiates into the two smaller petals, sometimes even to the edge. Occasionally, 1–2 additional small petals may develop. The flowers are long-lasting and non-dropping, and the seed capsule pushes slightly through.

I claim:

1. A new and distinct cultivar of African violet named Knoxville, as described and illustrated, and particularly characterized by its single, pink flowers with frilled edges and darker pink center radiating into the 2 smaller petals; strong, upright flower stems that curve toward the center to form a bouquet above the leaves; medium green, serrated girl-type leaves with bright light green center; profuse flowering, vigorous growth habit, flowering 10–11 weeks after potting, and its long-lasting and non-dropping flowers.

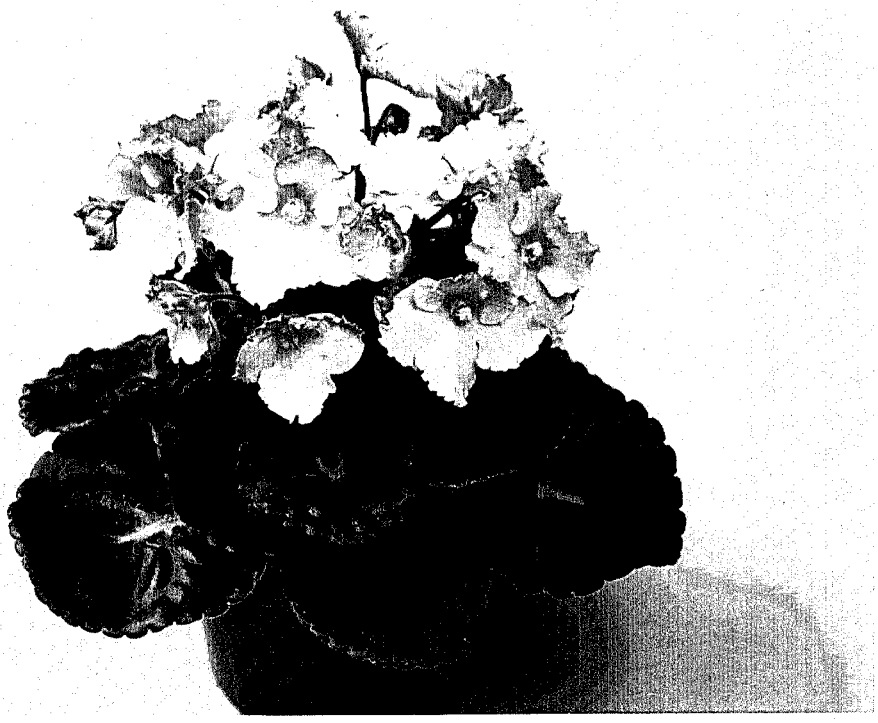

* * * * *